(12) United States Patent
Govari et al.

(10) Patent No.: US 10,709,472 B2
(45) Date of Patent: Jul. 14, 2020

(54) DEBRIDER WITH MULTIPLE FLUSHING ORIFICES

(71) Applicant: Biosense Webster (Israel) Ltd., Yokneam (IL)

(72) Inventors: Assaf Govari, Haifa (IL); Yaron Ephrath, Karkur (IL); Yehuda Algawi, Binyamina (IL); Ilya Sitnitsky, Nahariya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 247 days.

(21) Appl. No.: 15/264,341

(22) Filed: Sep. 13, 2016

(65) Prior Publication Data

US 2018/0070981 A1  Mar. 15, 2018

(51) Int. Cl.
| | | |
|---|---|---|
| A61B 17/3207 | (2006.01) | |
| A61B 17/32 | (2006.01) | |
| A61B 17/24 | (2006.01) | |
| A61M 1/00 | (2006.01) | |

(52) U.S. Cl.
CPC ...... *A61B 17/320783* (2013.01); *A61B 17/24* (2013.01); *A61B 17/32002* (2013.01); *A61B 17/320758* (2013.01); *A61B 2017/320032* (2013.01); *A61B 2017/320064* (2013.01); *A61B 2217/005* (2013.01); *A61B 2217/007* (2013.01)

(58) Field of Classification Search
CPC ........ A61B 17/32002; A61B 2217/007; A61B 17/320758; A61B 17/320783; A61M 1/0084; A61M 3/0283
See application file for complete search history.

(56) References Cited

U.S. PATENT DOCUMENTS

| | | | |
|---|---|---|---|
| 5,782,795 A * | 7/1998 | Bays | A61B 17/32002 |
| | | | 604/22 |
| 5,792,167 A | 8/1998 | Kablik et al. | |
| 6,183,433 B1 | 2/2001 | Bays | |
| 6,293,957 B1 | 9/2001 | Peters et al. | |
| 6,371,934 B1 | 4/2002 | Jackson et al. | |
| 8,162,966 B2 * | 4/2012 | Connor | A61B 17/320016 |
| | | | 606/160 |

(Continued)

FOREIGN PATENT DOCUMENTS

| | | |
|---|---|---|
| EP | 0174084 A2 | 3/1986 |
| EP | 2913012 A1 | 9/2015 |

(Continued)

OTHER PUBLICATIONS

Extended European Search Report dated Jan. 31, 2018 for Application No. 17190526.8, 10 pages.

*Primary Examiner* — Diane D Yabut
*Assistant Examiner* — Majid Jamialahmadi
(74) *Attorney, Agent, or Firm* — Frost Brown Todd LLC

(57) ABSTRACT

A surgical apparatus includes a debriding device, a hollow tube, and an irrigation assembly. The debriding device is fitted at a distal end of the surgical apparatus and is configured to debride tissue from a debriding site in a patient body. The hollow tube is configured to evacuate the debrided tissue away from the debriding site. The irrigation assembly is configured to apply irrigation fluid, via one or more orifices formed in the hollow tube, to the debrided tissue being evacuated.

15 Claims, 3 Drawing Sheets

(56) References Cited

U.S. PATENT DOCUMENTS

2011/0022069 A1* 1/2011 Mitusina .......... A61B 17/32002
　　　　　　　　　　　　　　　　　　　　　606/180
2014/0148729 A1　　5/2014　Schmitz et al.
2014/0148835 A1　　5/2014　Schmitz et al.
2016/0303310 A1* 10/2016 Dai ..................... A61M 3/0283

FOREIGN PATENT DOCUMENTS

WO　　WO 2012/058438 A1　　5/2012
WO　　WO 2014/145052 A1　　9/2014

* cited by examiner

DEBRIDER WITH MULTIPLE FLUSHING ORIFICES

FIELD OF THE INVENTION

The present invention relates generally to medical debriders, and particularly to methods and systems for irrigation in a debrider.

BACKGROUND OF THE INVENTION

Medical debriders are used in various procedures, such as in sinuplasty procedures carried out in a patient nose. Examples of prior art techniques for using debriders are provided below.

U.S. Pat. No. 6,371,934, whose disclosure is incorporated herein by reference, describes an irrigation system for removing arthritis-causing fragments from a joint in the body, the system includes a handpiece and a tip that is connectible to the handpiece. The tip includes a shaft that forms an irrigation lumen, and a debrider disposed along at least a part of the shaft. The debrider defines a substantially planar debriding surface for debriding the interior surfaces of the joint. The debrider may include a plurality of bristles extending from the shaft to the debriding surface.

U.S. Patent Application Publication 2014/0148835, issued as U.S. Pat. No. 9,814,484 on Nov. 14, 2017, whose disclosure is incorporated herein by reference, describes a bendable medical device that includes a distal housing, an outer support tube, an inner drive tube, a coupler and a commutator portion. The coupler and commutator portion serve to axially constrain a distal end of the inner drive tube during bending, and to supply fluid for lubricating, cooling and irrigating the distal end of the device.

U.S. Pat. No. 6,183,433, whose disclosure is incorporated herein by reference, describes a surgical suction cutting instrument with internal irrigation. The instrument includes a tubular outer member defining a cutting chamber with an opening, an inner member with a distal cutting edge movably received in the outer tubular member and a flushing mechanism for supplying fluid to the cutting chamber via an outlet communicating with the cutting chamber.

U.S. Patent Application Publication 2014/0148729, now abandoned, whose disclosure is incorporated herein by reference, describes a method for removing at least part of a brain tumor that may first involve contacting a forward-facing tissue cutter disposed at the distal end of a tissue removal device with the brain tumor. The tissue removal device may include a shaft having a diameter no greater than about 10 mm, and in some embodiments the tissue cutter does not extend laterally beyond the diameter of the shaft. The method may next involve cutting tissue from the brain tumor, using the tissue cutter. The method may then involve moving the cut tissue through a channel of the shaft in a direction from the distal end of the tissue removal device toward a proximal end of the device.

U.S. Pat. No. 6,293,957, whose disclosure is incorporated herein by reference, describes a method for performing sinus surgery that utilizes a sinus debrider instrument. The method includes the steps of positioning the distal end of the instrument at an operative site within the sinus, cutting tissue at the operative site within the sinus by rotating the tissue cutting surface, removing the cut tissue from the sinus through the suction passage and supplying fluid to the tissue cutting surface through the fluid passage to facilitate the removal of cut tissue without introducing fluid to the operative site.

SUMMARY OF THE INVENTION

An embodiment of the present invention that is described herein provides a surgical apparatus including a debriding device, a hollow tube, and an irrigation assembly. The debriding device is fitted at a distal end of the surgical apparatus and is configured to debride tissue from a debriding site in a patient body. The hollow tube is configured to evacuate the debrided tissue away from the debriding site. The irrigation assembly is configured to apply irrigation fluid, via one or more orifices formed in the hollow tube, to the debrided tissue being evacuated.

In some embodiments, each orifice is configured to regulate a selected irrigating pressure of the irrigation fluid delivered via the orifice. In other embodiments, the irrigation assembly is mounted inside the hollow tube. In yet other embodiments, the surgical apparatus includes a suction assembly, which is configured to assist in evacuating the debrided tissue by applying vacuum along the hollow tube.

In an embodiment, the surgical apparatus further includes a sleeve disposed around the hollow tube so as to form an intermediate lumen between the sleeve and an exterior of the hollow tube, and the irrigation assembly is configured to apply the irrigation fluid to the one or more irrigation orifices via the intermediate lumen. In another embodiment, the hollow tube is configured to rotate about its longitude axis so that at least a given orifice travels around an inner perimeter of the sleeve, such that the irrigation fluid is applied via the given orifice to multiple different locations distributed around the inner perimeter. In yet another embodiment, the sleeve includes an insertion tube for inserting the distal end into a patient body.

In some embodiments, the one or more orifices include multiple orifices that are distributed along the hollow tube. In other embodiments, the multiple orifices are configured to deliver the irrigation fluid at a same irrigation angle. In yet other embodiments, the multiple orifices include at least first and second orifices, such that the first orifice is located closer to the debriding device than the second orifice, and the irrigation assembly is configured to apply the irrigation via the second orifice to the debrided tissue that was previously irrigated via the first orifice.

In an embodiment, the irrigation assembly is configured to determine a distribution of irrigating pressures of the irrigation fluid along the hollow tube. In another embodiment, the multiple orifices include at least a first orifice, which is configured to apply the irrigation fluid at a first irrigation angle, and a second orifice, which is configured to apply the irrigation fluid at a second irrigation angle that is different from the first irrigation angle. In yet another embodiment, the hollow tube is perforated with one or more openings distributed along the hollow tube, and the irrigation assembly is coupled to an outer perimeter of the hollow tube so that each of the orifices is facing a respective one of the openings.

There is additionally provided, in accordance with an embodiment of the present invention, a surgical method including debriding tissue from a debriding site in a patient body. The debrided tissue is evacuated, through a hollow tube, away from the debriding site. Irrigation fluid is applied to the debrided tissue being evacuated via one or more orifices formed in the hollow tube.

There is additionally provided, in accordance with an embodiment of the present invention, a method for producing a surgical apparatus, the method includes fitting at a distal end of the surgical apparatus a debriding device, which is configured to debride tissue from a debriding site in a patient body. A hollow tube, which is configured to evacuate the debrided tissue away from the debriding site, is coupled to the debriding device. An irrigation assembly that is used for applying irrigation fluid to the debrided tissue being evacuated, via one or more orifices formed in the hollow tube, is fitted to the hollow tube.

The present invention will be more fully understood from the following detailed description of the embodiments thereof, taken together with the drawings in which:

DETAILED DESCRIPTION OF EMBODIMENTS

Overview

In various medical procedures, such as sinuplasty, a debriding catheter may be used for removing tissue from a human body. The catheter may comprise a cutter that removes the tissue and a hollow tube through which the debrided tissue is evacuated. In some cases, the debrided tissue may get stuck and clog the hollow tube during the evacuation, thus interrupting the medical procedure and possibly undesirably leaving at least some debrided tissue in the body.

It is possible in principle to apply irrigation at a single point close to the cutter, so as to wash out the debrided tissue during or shortly after cutting. Such irrigation, however, cannot prevent further clogging of debrided tissue that may occur at points further along the hollow tube, especially in case of large or rough debrided tissue.

Embodiments of the present invention that are described hereinbelow provide improved techniques for evacuating debrided tissue away from the human body. In the disclosed techniques, tissue evacuation is carried out by applying irrigation fluid to the debrided tissue using an irrigation assembly that includes one or more irrigating orifices. In a typical embodiment, multiple irrigating orifices are distributed along the hollow tube. Since irrigation is applied at multiple points along the tube, the likelihood of clogging further away from the cutter is reduced considerably.

In some embodiments, the irrigation assembly may determine the angle of irrigation from each orifice. In addition, the irrigation assembly may control the pressure of irrigation as applied from every individual orifice, or a group of orifices, into the hollow tube. In other embodiments, the irrigation assembly may apply the fluid continuously into the hollow tube while the fluid and the debrided tissue are continuously evacuated away from the human body.

The disclosed irrigation assembly allows reliable evacuation of the debrided tissue along the tube using multiple distributed irrigating orifices. Furthermore, the disclosed techniques allow the removal of multiple selected pieces of tissue during a single procedure, therefore avoiding the need for retracting the catheter for cleaning after removing one or more pieces of debrided tissue.

System Description

Figure 1:
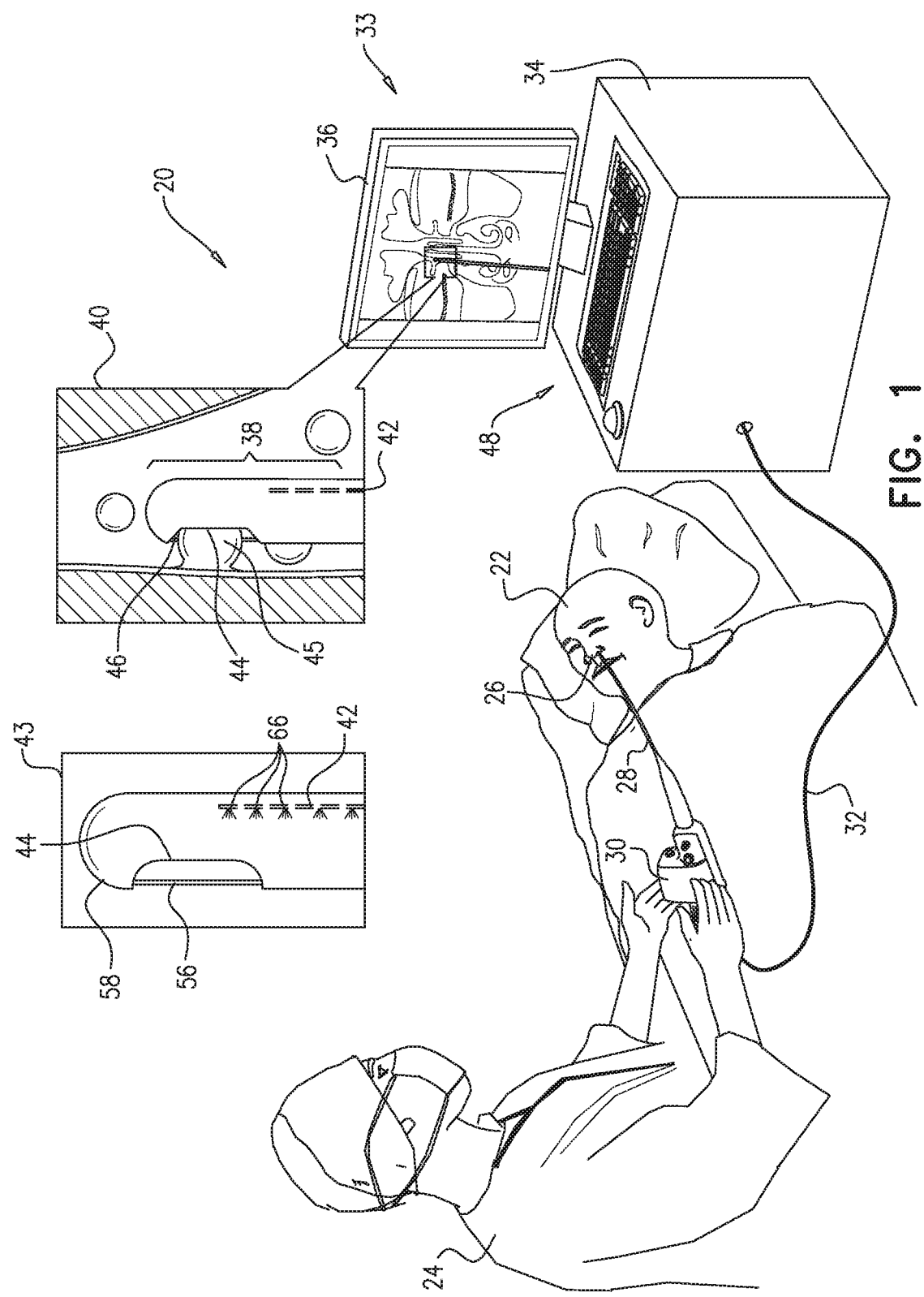
FIG. 1 is a schematic pictorial illustration of a sinuplasty procedure using a surgical system, in accordance with an embodiment of the present invention.

FIG. 1 is a schematic pictorial illustration of a sinuplasty procedure using a surgical system 20, in accordance with an embodiment of the present invention. System 20 comprises a catheter 28, which a physician 24 inserts into a nose 26 of a patient 22 so as to remove tissue, such as a nasal polyp 45 (shown in an inset 40) at a debriding site. Catheter 28 comprises a proximal end 30, configured to control a distal end 38 of the catheter.

System 20 further comprises a console 33, which comprises a processor 34, typically a general-purpose computer, with suitable front end and interface circuits for receiving signals from catheter 28, via a cable 32, and for controlling other components of system 20 described herein. Console 33 further comprises input devices 48 and a display 36, which are configured to display data received from processor 34 and receive inputs inserted by a user (e.g., physician 24).

Reference is now made to insets 40 and 43, distal end 38 typically comprises a rigid hollow insertion tube 58 for insertion into the nose of patient 22. Tube 58 is coaxially disposed around a rotating shaft 56 (shown in greater detail in FIG. 2). Shaft 56 may be driven using any suitable mechanism, such as a direct current (DC) motor that can rotate clockwise and counterclockwise depending on the polarity of the electrical current applied to the motor.

In some embodiments, tube 58 has an opening 44. Shaft 56 comprises a debriding device such as a sinuplasty cutter 46 that is aligned with opening 44 in the insertion tube. Cutter 46 is configured to rotate together with the shaft so as to cut polyp 45.

Reference is now made to inset 40. During the sinuplasty procedure, physician 24 navigates catheter 28 so that opening 44 is facing the debriding site (e.g., polyp 45). In other embodiments, catheter 28 may apply suction for pulling polyp 45 therein, and cutter 46 does not block opening 44 so that polyp 45 may be inserted through opening 44 into tube 58. Once polyp 45 passes through opening 44, physician 24 may use console 33 or proximal end 30 to rotate shaft 56 including cutter 46 so as to remove at least part of polyp 45.

Catheter 28 evacuates the removed polyp into a drain (not shown) located, for example, in proximal end 30. Sometimes, after being removed by cutter 46, polyp 45 may get stuck and cause clogging at any point along tube 58. In some embodiments, system 20 comprises an irrigation assembly 42, mounted along an inner perimeter of tube 58. Irrigation assembly 42 is configured to irrigate the removed polyp by applying fluid 66 via one or more orifices, e.g., multiple orifices distributed along cutter 46 and tube 58 so as to evacuate the debrided polyp and prevent clogging of tube 58.

In another embodiment, catheter 28 may apply fluid suction, in conjunction with the irrigation, so as to improve the evacuation of fluid 66 together with the debrided polyp. The suction may be carried out using an internal vacuum pump (not shown) located at proximal end 30 or at console 33. Assembly 42 is further described in FIG. 2 below.

FIG. 1 shows only elements related to the disclosed techniques, for the sake of simplicity and clarity. System 20 typically comprises additional modules and elements that are not directly related to the disclosed techniques, and thus, intentionally omitted from FIG. 1 and form the corresponding description.

Alternatively, some or all of the functions of processor 34 may be carried out by dedicated or programmable digital hardware components.

Irrigation of Sinuplasty Cutter

A sinuplasty procedure typically involves inserting catheter 28, e.g., into the patient nose, navigating it to the location of polyp 45 (or any other tissue), and removing the polyp (or other tissue) using a debriding device such as cutter 46. Sometimes, the removed polyp (or other tissue) may be large and/or have rough texture so that it may get stuck at any point along tube 58, thus clogging the tube and interrupting the sinuplasty procedure.

In principle, it is possible to apply irrigation only close to cutter 46 during the cutting process, but such a solution may not prevent clogging at points further along tube 58, even if irrigation was already applied upstream (e.g., close to cutter 46). The disclosed techniques reduce or eliminate clogging of tube 58, by applying pressurized irrigation fluid at one or more points in tube 58, thereby securing the evacuation of the debrided tissue.

Figure 2:
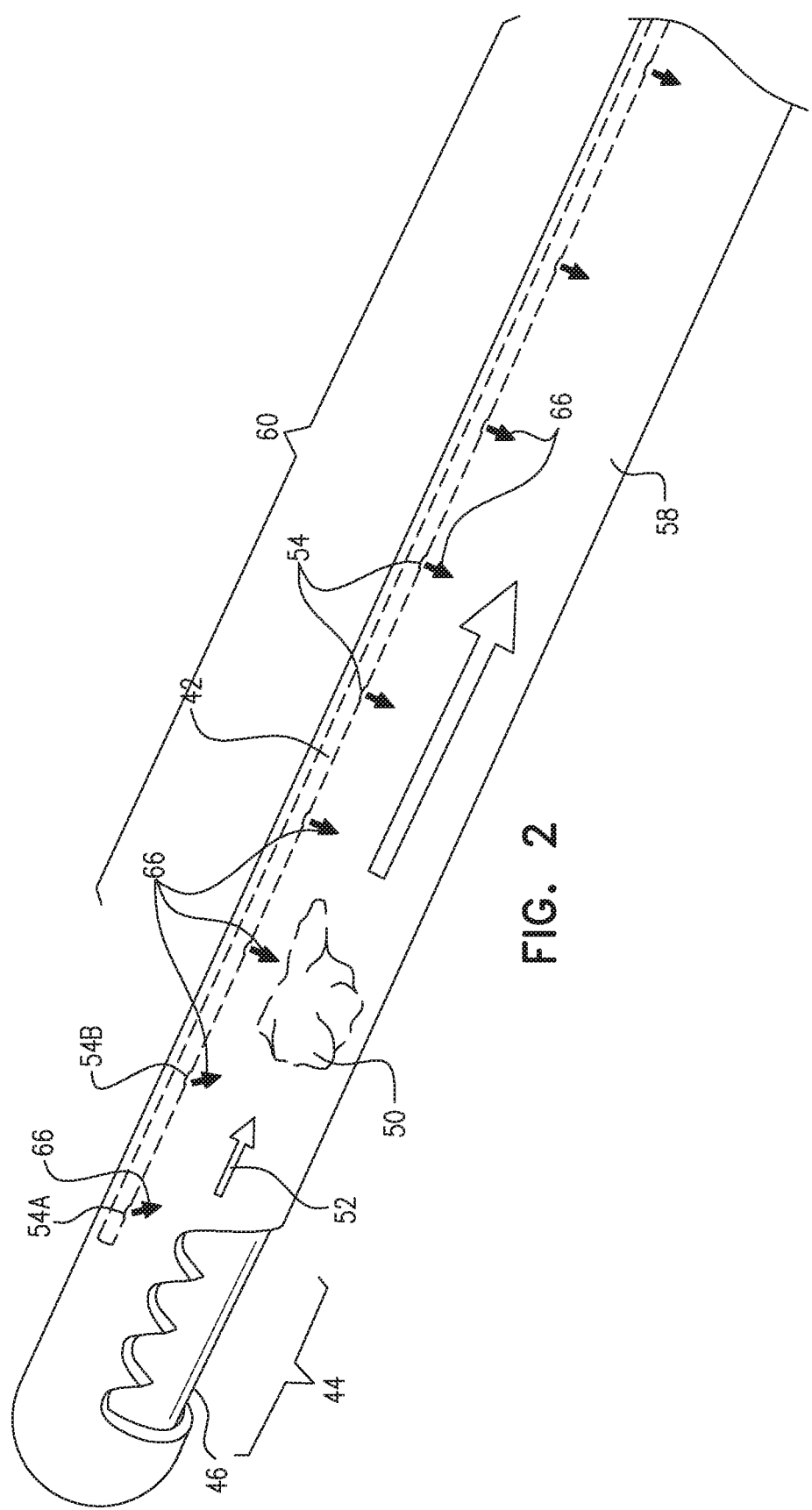
FIG. 2 is a schematic side view of a distal end of a debrider used in a sinuplasty surgical system, in accordance with an embodiment of the present invention.

FIG. 2 is a schematic side view of distal end 38, in accordance with an embodiment of the present invention. Distal end 38 comprises cutter 46 and irrigation assembly 42 as described above. Irrigation assembly 42 comprises multiple irrigation orifices 54, 54A and 54B located along assembly 42. Orifices 54A and 54B are located in proximity to cutter 46, and orifices 54 are grouped in a group 60 and located along distal end 38, as shown in FIG. 2, and may continue along catheter 28 further away from cutter 46.

Each orifice (e.g., 54A, 54B and 54) is configured to deliver pressurized fluid 66 into the internal lumen of tube 58 at a desired configurable delivery angle. In the example of FIG. 2, orifices 54 are configured to deliver fluid 66 orthogonally to assembly 42 while orifices 54A and 54B are configured to deliver fluid 66 at a non-orthogonal angle. In alternative embodiments, all the orifices may deliver fluid at a substantially similar selected angle.

In the example of FIG. 2, a debris 50 represents the removed portion of polyp 45, or any other tissue being evacuated. In some embodiments, pressurized fluid 66 carries debris 50 (represented by arrows 52) away from cutter 46, along tube 58, toward proximal end 30. In other embodiments, system 20 may apply a suction force (e.g., using a vacuum pump) in catheter 28 so as to pull debris 50 and fluid 66 toward proximal end 30. The suction force is typically moderate so as to prevent opening 44 from undesirably sticking to tissue because of the applied suction force.

In an embodiment, assembly 42 may control the delivery pressure or fluid 66 from each individual orifice. For example, orifice 54A may deliver fluid 66 at a higher pressure level than orifice 54B. In another embodiment, each orifice is configured to deliver fluid 66 at a predefined selected pressure. Thus, assembly 42 maintains sufficiently large internal pressure of fluid 66 so that all orifices, including the proximal (e.g., orifices 54) and distal orifices (e.g., 54A, 54B), deliver the fluid at a substantially uniform pressure.

In the example of FIG. 2, irrigation assembly 42 is laid on the inside of tube 58, along the length of the tube. In alternative embodiments, assembly 42 may have various other configurations and may be coupled to tube 58 in various other locations. For example, assembly 42 may by wrapped around the inner perimeter of tube 58 so that the orifices are mounted in a cascading arrangement around the inner perimeter of insertion tube 58 rather than arranged in line as depicted in FIG. 2. This arrangement may assist in decoupling portions of debris 50 that may undesirably adhere to specific locations along the inner perimeter of tube 58.

In other embodiments, the wall of tube 58 may be perforated and assembly 42 may be coupled on an outer perimeter of tube 58 so that each orifice (e.g., 54, 54A and 54B) is arranged in front of a respective hole from which it delivers fluid 66 into the internal lumen of tube 58.

Figure 3:
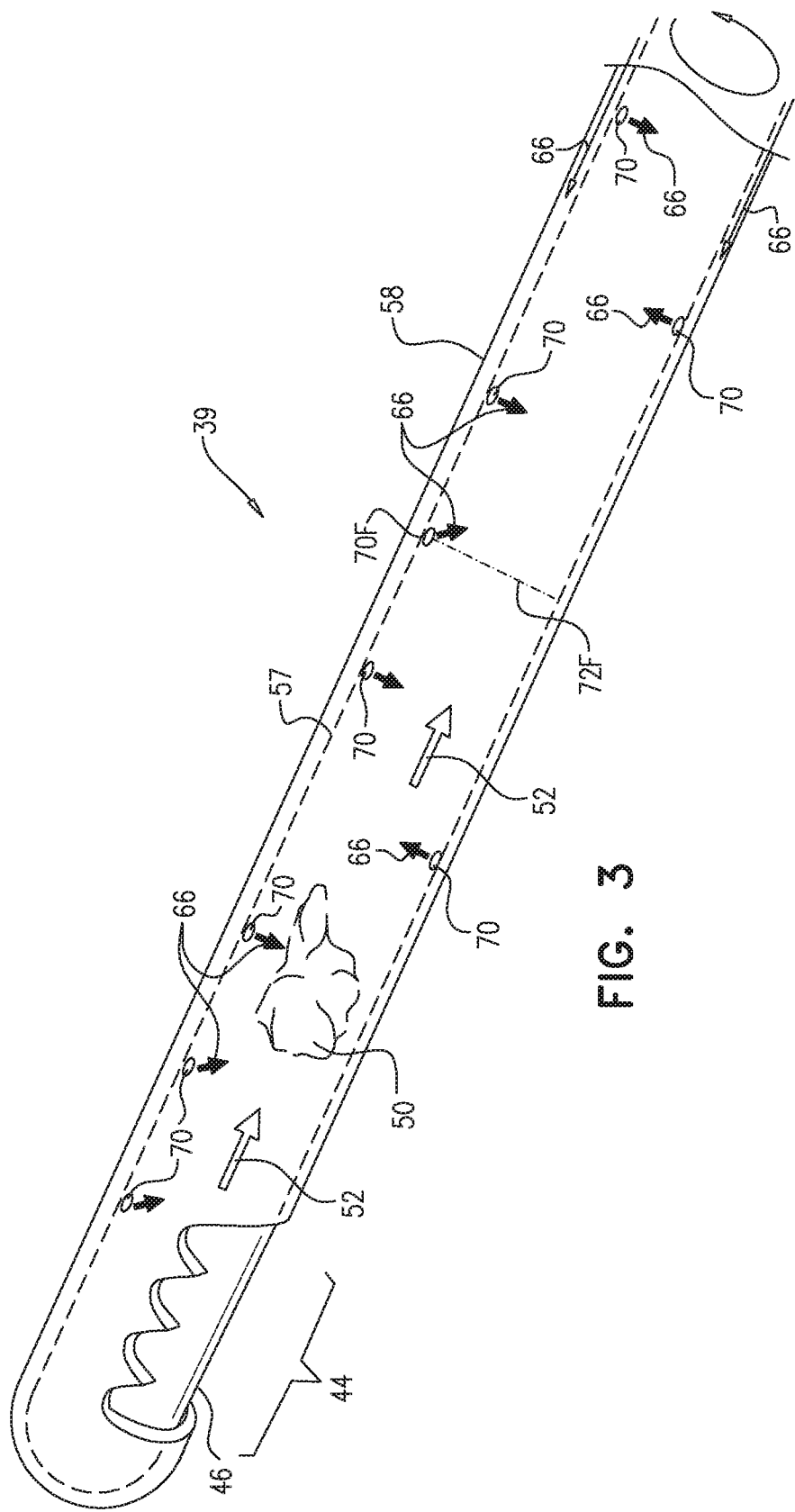
FIG. 3 is a schematic side view of a distal end of a debrider used in a sinuplasty surgical system, in accordance with another embodiment of the present invention.

FIG. 3 is a schematic side view of a distal end 39, in accordance with another embodiment of the present invention. Distal end 39 may be used, for example, to implement distal end 38 of FIG. 1 above. In some embodiments, the distal end comprises tube 58 that is coaxially disposed around a rotating shaft 57, which is similar to shaft 56 of FIG. 1 above. Unlike shaft 56, however, shaft 57 is perforated by multiple irrigation orifices 70 that may be located at any suitable location along shaft 57. In an embodiment, shaft 57 is coupled to cutter 46 so that the shaft and cutter rotate together. Distal end 39 is configured to apply a suction force to draw fluid 66 that enters the shaft lumen via orifices 70 in the direction of arrows 52, so as to evacuate debris 50 toward the proximal end, through the internal lumen of shaft 57.

During operation, fluid 66 flows through a lumen that is formed between the inner surface of tube 58 and the outer surface of shaft 57, in the direction from the proximal end to distal end 39. Shaft 57 rotates about its longitude axis (i.e., in parallel to arrows 52) so that each of orifices 70 rotates around the inner perimeter of tube 58. For example, orifice 70F rotates along a circle 72F. Furthermore, each of orifices 70 is configured to deliver fluid 66 into the internal lumen of shaft 57 during the orifice travel along its circle at any desired delivery angle relative to the rotational axis.

The examples above refer to specific configurations of irrigation module 42 shown in FIGS. 1 and 2, and shaft 57 shown in FIG. 3, and are chosen purely for the sake of conceptual clarity. In alternative embodiments, any other suitable configuration can be used. For example, the debriding device need not necessarily comprise a rotating cutter, but may alternatively comprise a scissor-shaped surgical device. Further alternatively the debriding device may comprise a cutter that travels linearly toward the distal tip so as to cut polyp 45, and retracted linearly toward the proximal end so as to allow insertion of a new object to be cut into opening 44.

In alternative embodiments, the disclosed techniques can be used, mutatis mutandis, in various other types of surgical procedures in which tissue is cut and then evacuated using a suction catheter.

For example, debriding may be applied to some external surface of the patient body. The external debriding and irrigating to the surface tissue is carried out similarly to the procedures described above but without inserting tube 58 into the patient body.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

What is claimed is:

1. A surgical apparatus, comprising:
   (a) a debriding device, which is fitted at a distal end of the surgical apparatus and is configured to debride tissue from a debriding site in a patient body;
   (b) a hollow tube, configured to evacuate the debrided tissue away from the debriding site, wherein the hollow tube includes an inner surface; and
   (c) an irrigation assembly, configured to apply irrigation fluid, via one or more orifices, to the debrided tissue being evacuated, the irrigation assembly comprising an elongate member, wherein an outer surface of the elongate member is fixably coupled to the inner surface of the hollow tube to prevent relative movement between the elongate member and the hollow tube, wherein the one or more orifices are formed in the elongate member,
   wherein the one or more orifices comprise multiple orifices that are distributed along the elongate member, wherein the multiple orifices comprise at least first and second orifices, wherein the first orifice is configured to apply the irrigation fluid at a first irrigation angle, wherein the second orifice is configured to apply the irrigation fluid at a second irrigation angle that is different from the first irrigation angle, wherein the second irrigation angle is orthogonal to a longitudinal axis of the hollow tube.

2. The apparatus according to claim 1, wherein each orifice is configured to regulate a selected irrigating pressure of the irrigation fluid delivered via the orifice.

3. The apparatus according to claim 1, and comprising a suction assembly, which is configured to assist in evacuating the debrided tissue by applying vacuum along the hollow tube.

4. The apparatus according to claim 1, wherein the first orifice is located closer to the debriding device than the second orifice, and wherein the irrigation assembly is configured to apply the irrigation via the second orifice to the debrided tissue that was previously irrigated via the first orifice.

5. The apparatus according to claim 4, wherein the first irrigation angle is non-orthogonal to the longitudinal axis of the hollow tube.

6. The apparatus according to claim 1, wherein the irrigation assembly is configured to determine a distribution of irrigating pressures of the irrigation fluid along the hollow tube.

7. The apparatus according to claim 1, wherein the multiple orifices are arranged in a line.

8. The apparatus according to claim 1, wherein the elongate member is an elongate tube that is configured to circumferentially surround the irrigation fluid, wherein the one or more orifices are formed in the elongate tube.

9. The apparatus according to claim 1, wherein the hollow tube defines an internal lumen extending along a central axis, wherein the elongate member is laterally offset from the central axis within the internal lumen.

10. The apparatus according to claim 1, wherein the elongate member and the hollow tube are non-concentric.

11. A surgical apparatus, comprising:
    (a) a debriding device, which is fitted at a distal end of the surgical apparatus and is configured to debride tissue from a debriding site in a patient body;
    (b) a hollow tube, configured to evacuate the debrided tissue away from the debriding site, the hollow tube defining an internal lumen extending along a central axis; and
    (c) an irrigation assembly, configured to apply irrigation fluid, via one or more orifices, to the debrided tissue being evacuated, the irrigation assembly being positioned inside of the hollow tube, the irrigation assembly comprising an elongate tube that is laterally offset from the central axis within the internal lumen, wherein the elongate tube is configured to circumferentially surround the irrigation fluid, wherein the one or more orifices are formed in the elongate tube,
    wherein the one or more orifices comprise multiple orifices that are distributed along the elongate tube, wherein the multiple orifices comprise at least first and second orifices, wherein the first orifice is configured to apply the irrigation fluid at a first irrigation angle, wherein the second orifice is configured to apply the irrigation fluid at a second irrigation angle that is different from the first irrigation angle, wherein the second irrigation angle is orthogonal to the central axis of the hollow tube.

12. The apparatus according to claim 11, wherein the elongate tube and the hollow tube are non-concentric.

13. A surgical apparatus, comprising:
    (a) a hollow tube configured to evacuate tissue away from a debriding site, wherein the hollow tube defines an internal lumen extending along a central axis;
    (b) an elongate shaft disposed within the internal lumen, wherein the elongate shaft comprises a debriding device that is fitted at a distal end of the elongate shaft and is configured to debride the tissue from the debriding site in a patient body; and
    (c) an irrigation assembly that includes an elongate tube that is laterally offset from the central axis within the internal lumen, the irrigation assembly being positioned inside of the hollow tube, wherein the irrigation assembly includes at least first and second orifices configured to apply irrigation fluid to the debrided tissue being evacuated, wherein the first orifice is configured to apply the irrigation fluid at a first irrigation angle, wherein the first irrigation angle is orthogonal to the central axis of the hollow tube.

14. The apparatus according to claim 13, wherein the hollow tube is straight, wherein the central axis runs along the entire length of the hollow tube.

15. The apparatus according to claim 13, wherein the first orifice located is closer to the debriding device than the second orifice, and wherein the second orifice is configured to apply the irrigation fluid to the debrided tissue that was previously irrigated via the first orifice.

* * * * *